US011213806B1

(12) United States Patent
Bhasin

(10) Patent No.: US 11,213,806 B1
(45) Date of Patent: Jan. 4, 2022

(54) CATALYST SUPPORTS—COMPOSITION AND PROCESS OF MANUFACTURE

(71) Applicant: Mid-Atlantic Technology, Research & Innovation Center, Inc., South Charleston, WV (US)

(72) Inventor: Madan Bhasin, Charleston, WV (US)

( * ) Notice: Subject to any disclaimer, the term of this patent is extended or adjusted under 35 U.S.C. 154(b) by 0 days.

(21) Appl. No.: 16/448,632

(22) Filed: Jun. 21, 2019

Related U.S. Application Data

(60) Provisional application No. 62/688,236, filed on Jun. 21, 2018.

(51) Int. Cl.
| | |
|---|---|
| *B01J 27/224* | (2006.01) |
| *B01J 35/10* | (2006.01) |
| *B01J 37/08* | (2006.01) |
| *B01J 35/02* | (2006.01) |
| *B01J 23/50* | (2006.01) |
| *B01J 37/02* | (2006.01) |
| *C07D 301/06* | (2006.01) |
| *C10G 45/04* | (2006.01) |
| *C10G 11/02* | (2006.01) |
| *C07C 5/333* | (2006.01) |
| *C10G 47/02* | (2006.01) |

(52) U.S. Cl.
CPC ............ *B01J 27/224* (2013.01); *B01J 23/50* (2013.01); *B01J 35/023* (2013.01); *B01J 35/1009* (2013.01); *B01J 35/1014* (2013.01); *B01J 35/1038* (2013.01); *B01J 35/1042* (2013.01); *B01J 37/0203* (2013.01); *B01J 37/08* (2013.01); *C07C 5/3335* (2013.01); *C07D 301/06* (2013.01); *C10G 11/02* (2013.01); *C10G 45/04* (2013.01); *C10G 47/02* (2013.01); *C07C 2521/08* (2013.01); *C07C 2521/18* (2013.01); *C07C 2523/50* (2013.01); *C10G 2300/202* (2013.01); *C10G 2300/207* (2013.01)

(58) Field of Classification Search
CPC ...... B01J 27/224; B01J 37/0203; B01J 37/08; B01J 35/1038; B01J 35/1042; B01J 23/50; B01J 35/023; B01J 35/10009; B01J 35/1014; C01G 11/02; C01G 47/02; C07D 301/06; C07C 5/3335; C07C 2521/08; C07C 2521/18; C07C 2523/50; C10G 2300/207; C10G 2300/202
USPC .......................................... 549/533; 502/178
See application file for complete search history.

(56) References Cited

U.S. PATENT DOCUMENTS

| | | |
|---|---|---|
| 244,438 A | 7/1881 | Dodge |
| 410,115 A | 8/1889 | Reed |
| 2,040,782 A | 5/1936 | Johannes |
| RE20,370 E | 5/1937 | Lefort |
| 2,177,361 A | 10/1939 | Carter |
| 2,238,471 A | 4/1941 | Keyasner et al. |
| 2,238,474 A | 4/1941 | McNamee et al. |
| 2,294,383 A | 9/1942 | Carter |
| 2,424,084 A | 7/1947 | Finch et al. |
| 2,424,086 A | 7/1947 | Bergsteinsson et al. |
| 2,459,896 A | 1/1949 | Schwarz |
| 2,463,228 A | 3/1949 | West et al. |
| 2,477,435 A | 7/1949 | Aries |
| 2,554,459 A | 5/1951 | Heider |
| 2,615,900 A | 10/1952 | Sears, Jr. |
| 2,671,764 A | 3/1954 | Sacken |
| 2,709,173 A | 5/1955 | Brengle et al. |
| 2,765,283 A | 10/1956 | Sacken |
| 2,766,261 A | 10/1956 | Landau |
| 2,769,016 A | 10/1956 | Lichtenwalter et al. |
| 2,773,844 A | 12/1956 | Carlson et al. |
| 2,799,687 A | 7/1957 | Gould et al. |
| 2,825,701 A | 3/1958 | Endler et al. |
| 2,831,870 A | 4/1958 | McClements et al. |

(Continued)

FOREIGN PATENT DOCUMENTS

| | | |
|---|---|---|
| CA | 1048010 A | 2/1979 |
| CA | 1117515 A | 2/1982 |

(Continued)

OTHER PUBLICATIONS

Lee et al , Support and crystallite size effects in ethylene oxidation, Applied Catalysis, vol. 50, issue 1, May 1, 1989, p. 171-188, (abstract) (Year: 1989).*

(Continued)

*Primary Examiner* — Taylor V Oh

(74) *Attorney, Agent, or Firm* — Dinsmore & Shohl LLP; Monika Jaensson

(57) ABSTRACT

A catalyst support comprising at least 95% silicon carbide, having surface areas of ≤10 m²/g and pore volumes of ≤1 cc/g. A method of producing a catalyst support, the method including mixing SiC particles of 0.1-20 microns, $SiO_2$ and carbonaceous materials to form an extrusion, under inert atmospheres, heating the extrusion at temperatures of greater than 1400° C., and removing residual carbon from the heated support under temperatures below 1000° C. A catalyst on a carrier, comprising a carrier support having at least about 95% SiC, with a silver solution impregnated thereon comprising silver oxide, ethylenediamine, oxalic acid, monoethanolamine and cesium hydroxide. A process for oxidation reactions (e.g., for the production of ethylene oxide, or oxidation reactions using propane or methane), or for endothermic reactions (e.g., dehydrogenation of paraffins, of ethyl benzene, or cracking and hydrocracking hydrocarbons).

3 Claims, No Drawings

(56) References Cited

U.S. PATENT DOCUMENTS

| | | | |
|---|---|---|---|
| 2,901,441 A | 8/1959 | Waterman | |
| 3,125,538 A | 3/1964 | Arnold et al. | |
| 3,140,253 A * | 7/1964 | Plank | B01J 29/082 208/120.15 |
| 3,144,416 A | 8/1964 | Hosoda et al. | |
| 3,144,916 A | 8/1964 | Lien | |
| 3,166,380 A * | 1/1965 | Kuhn | C01B 32/97 423/346 |
| 3,172,893 A | 3/1965 | Ameen | |
| 3,207,700 A | 9/1965 | Saffer | |
| 3,258,433 A | 6/1966 | Lambert et al. | |
| 3,332,887 A | 7/1967 | Endler | |
| 3,420,784 A | 1/1969 | Hindin et al. | |
| 3,423,328 A | 1/1969 | Keith et al. | |
| 3,501,407 A | 3/1970 | Akashi et al. | |
| 3,501,417 A | 3/1970 | DeMaio | |
| 3,563,913 A | 2/1971 | de Krijger et al. | |
| 3,563,914 A | 2/1971 | Wattimena | |
| 3,585,217 A | 6/1971 | Titzenthaler | |
| 3,664,970 A | 5/1972 | De Maio | |
| 3,702,259 A | 11/1972 | Nielsen | |
| 3,725,307 A | 4/1973 | Brown et al. | |
| 3,758,418 A | 9/1973 | Leonard et al. | |
| 3,844,981 A | 10/1974 | Cusumano | |
| 3,962,136 A | 6/1976 | Nielsen et al. | |
| 3,962,285 A | 6/1976 | Cusumano | |
| 4,010,115 A | 3/1977 | Nielsen et al. | |
| 4,012,425 A | 3/1977 | Nielsen et al. | |
| 4,033,903 A | 7/1977 | Maxwell | |
| 4,039,561 A | 8/1977 | Mitsuhata et al. | |
| 4,066,575 A | 1/1978 | Winnick | |
| 4,097,414 A | 6/1978 | Cavitt | |
| 4,125,480 A | 11/1978 | Maxwell | |
| 4,212,772 A | 7/1980 | Mross et al. | |
| 4,761,394 A | 8/1988 | Lauritzen | |
| 4,766,105 A | 8/1988 | Lauritzen | |
| 4,820,675 A | 2/1989 | Lauritzen | |
| 4,833,261 A | 5/1989 | Lauritzen | |
| 4,908,343 A | 3/1990 | Bhasin | |
| 4,916,243 A | 4/1990 | Bhasin et al. | |
| 4,994,589 A * | 2/1991 | Notermann | B01J 23/66 549/534 |
| 5,057,481 A | 10/1991 | Bhasin | |
| 5,093,535 A * | 3/1992 | Harrison | C07C 29/141 568/881 |
| 6,133,184 A * | 10/2000 | Kiyooka | B01J 23/22 502/63 |
| 6,511,938 B1 | 1/2003 | Liu et al. | |
| 2011/0150741 A1 * | 6/2011 | Lang | C01B 33/025 423/345 |
| 2014/0323295 A1 * | 10/2014 | Shibata | C07D 301/10 502/347 |
| 2015/0337207 A1 * | 11/2015 | Chen | C10G 51/026 585/240 |
| 2016/0369191 A1 * | 12/2016 | Ward | C10G 67/0445 |

FOREIGN PATENT DOCUMENTS

| | | | |
|---|---|---|---|
| CN | 103496703 | * | 10/2013 |
| DE | 2640540 A1 | | 3/1978 |
| EP | 0003642 A2 | | 8/1979 |
| EP | 0085237 A1 | | 10/1983 |
| EP | 0247414 A2 | | 2/1987 |
| EP | 0266015 A1 | | 10/1987 |
| EP | 0266852 A1 | | 11/1988 |
| GB | 2002252 A | | 2/1979 |
| JP | S56105750 A | | 8/1981 |
| JP | H0985096 | * | 3/1997 |
| JP | 5721937 B2 | | 5/2015 |
| WO | WO2014/140973 | * | 9/2014 |

OTHER PUBLICATIONS

Zhong et al, Synthesis of Silicon Carbide Nanopowder Using Silica fume, J. Am. Ceram. Soc., 93 [10] 3159-3167 (2010). (Year: 2010).*

Moene et al, High surface area silicon carbide as catalyst support characterization and stability, Applied Catalysis A: General 167 (1998) 321-330). (Year: 1998).*

Sundaram, "Kirk-Othmer Encyclopedia of Chemical Technology 4th. Ed. vol. No. 9", 1994, 46 pgs.

Lee et al. "Support and Crystallite Size Effects in Ethylene Oxidation Catalysis" Applied Catalysis, 50 (1989) 171-188, 18 pgs.

Lee et al. "Support Participation in Chemistry of Ethylene Oxidation on Silver Catalysts" Applied Catalysis, 44 (1988) 223-237, 15 pgs.

Pugh, Surface Chemical Analysis of Oxidized Ultrafine α-SiC Powders by Electron Spectroscopy, Journal of Colloid and Interface Science, vol. 138, No. 1, Aug. 1990, pp. 16-20.

* cited by examiner

CATALYST SUPPORTS—COMPOSITION AND PROCESS OF MANUFACTURE

BACKGROUND

The disclosed technology regards a silicon carbide catalyst support or carrier which may be impregnated by a silver catalyst, and when so impregnated is useful in processes such as the selective oxidation of ethylene to ethylene oxide and other selective oxidation reactions, such as oxydehydrogenation of ethane, propane to produce corresponding olefins, nitriles, acids, etc., methane oxidative coupling to make ethylene, propylene, ethane, and other desired products. The disclosed technology further regards a method of producing a silicon carbide catalyst support, a silver catalyst on a silicon carbide catalyst support, and a process for a selective oxidation reaction, such as the production of ethylene oxide, using ethylene and $O_2$ as reactants over a silicon carbide catalyst support impregnated with a silver catalyst.

Selective oxidation reactions, such as oxydehydrogenation of ethane, propane to produce corresponding olefins, nitriles, acids, etc., and methane oxidative coupling to make ethylene, propylene, ethane, and other desired products, include the reaction of oxygen or oxygen-containing gases with the corresponding ethane, propane or methane, in the presence of suitable catalysts known for each oxidation reaction. Another suitable use of such catalyst supports is in the exothermic hydrogenation reactions and hydrodesulfurizations of various light and heavy hydrocarbon feed stocks.

Similarly, the novel catalyst supports are also beneficial for endothermic reactions, such as dehydrogenation of various paraffins, very important industrial reactions such as propane, butanes, and higher linear paraffins, C-9 to C-14; dehydrogenation of ethyl benzene to styrene; and cracking and hydrocracking of heaver hydrocarbons to lighter ones for fuels.

Among the oxidation reactions, in the manufacture of ethylene oxide by the reaction of oxygen or oxygen-containing gases with ethylene in the presence of a silver catalyst is an old and very well developed art. For example, U.S. Pat. No. 2,040,782, issued May 12, 1936, describes the manufacture of ethylene oxide by the reaction of oxygen with ethylene in the presence of silver catalysts which contain a class of metal promoters. In U.S. Pat. No. Re. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

In characterizing this invention, the terms "conversion", "selectivity", and "yield" are employed as defined in U.S. Pat. No. 3,420,784, patented Jan. 7, 1969, at column 3, lines 24-35 inclusive. This definition of "selectivity" is consistent with that disclosed in U.S. Pat. No. 2,766,261 at column 6, lines 5-22, and U.S. Pat. No. 3,144,916, lines 58-61. The definitions of "yield" and "conversion" have more varied meaning in the art and are not to be employed as defined, for example, in the aforementioned U.S. Pat. No. 2,766,261. The terms "efficiency" and "selectivity" as used throughout the specification and claims are intended to be synonymous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalysts are shaped particulate materials which can be loaded in the interior of a reactor wherein the reacting gases and the gaseous products of the reaction are capable of flowing in and about these particulate materials to pass through the reactor and be recovered. The size and shape of the support are variable factors and the particular size and shape selected are peculiar to the reactor employed, the gas flow required, and the surface area which is desired for the optimization of the reaction with other factors also being considered.

The carriers that have been employed are typically made of inorganic materials, generally of a mineral nature. In most cases, the preferred carrier is made of alpha-alumina, such as has been described in the patent literature: see for example, U.S. Pat. Nos. 2,294,383; 3,172,893; 3,332,887; 3,423,328; and 3,563,914.

Critical to making a carrier which proves uniquely desirable for the manufacture of a successful catalyst can be a number of factors, such as the purity and other physical/chemical properties of raw materials used to make the carrier and the method by which the carrier is made.

The silver that is deposited on these carriers is typically in the form of small particles. The patent literature indicates that the size of the silver is a factor in the effectiveness of the catalyst and in most cases fine particle silver is obtained utilizing the standard processes in the art; see, for example, U.S. Pat. Nos. 2,554,459; 2,831,870; 3,423,328 (specifies that silver particles of 150-400 Angstroms are employed); U.S. Pat. No. 3,702,259 (disclosed a preparation procedure for forming silver particles less than 1 micron in diameter); and U.S. Pat. No. 3,758,418 (discloses silver particles having a diameter less than 1000 angstroms).

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and, in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U.S. patents such as U.S. Pat. Nos. 2,773,844; 3,207,700; 3,501,407; and 3,664,970 (see British Patent No. 754,593), and U.S. Pat. No. 3,172,893.

The surface area provided by the support has been the subject of considerable interest in the development of silver catalysts. Disclosures concerning the surface area of the catalyst carrier can be found in U.S. Pat. No. 2,766,261 (which discloses that a surface area of 0.002-10 $m^2/gm$ is suitable); U.S. Pat. No. 3,172,893 (which depicts a porosity of 35-65% and a pore diameter of 80-200 microns); U.S. Pat. No. 3,725,307 (which depicts a surface area of less than 1 $m^2/gm$ and an average pore diameter of 10-15 microns); U.S. Pat. No. 3,664,970 (which utilizes a support having a minimum porosity of about 30%, at least 90% of the pores having diameters in the range of 1-30 microns, and the average of such diameters being in the range of 4-10 microns); and U.S. Pat. No. 3,563,914 (which utilizes a catalyst support having a surface area of less than 1 $m^2/gm$, a volume of 0.23 ml/gm and a particle size between 0.074 and 0.30 mm). Low surface area, inert alpha alumina is favored by the prior art.

In the very earliest developments of silver catalysts for the manufacture of ethylene oxide, it has been determined that a number of metals when present in combination with the silver could act as promoters of the silver catalyst. These materials in themselves are not catalysts but contribute to enhance the rate or amount of oxide production. One of the problems in determining whether or not these metals act as promoters is the nature of the reaction itself. The reaction between oxygen and ethylene to form ethylene oxide is a highly exothermic reaction. However, even more exothermic than that reaction is the combustion of ethylene or ethylene oxide to carbon dioxide. These reactions occur simultaneously and the critical factor in determining the effectiveness of the over-all process is the measure of control one has over these two competing reactions. Inevitably, a material which enhances the production of ethylene oxide might also be considered a material which inhibits the complete combustion of ethylene to ethylene oxide to carbon dioxide. Thus, there is a problem in defining whether that material which is termed as a promoter is in fact an inhibitor of the combustion reaction. It is well known that there are materials which when added to the reaction result in less carbon dioxide being formed and such materials are termed inhibitors. There are also materials which when provided with the catalysts result in greater production of ethylene oxide and those materials are termed promoters. Whether the latter materials are in reality inhibitors or promoters seems to be an irrelevant issue. What is significant is that the outcome of the reaction is favorable to the production of ethylene oxide. For that reason, when determining or characterizing a catalytic process for producing ethylene oxide a significant factor entering into or qualifying that process is the selectivity of the process to produce ethylene oxide, selectivity being as defined previously.

The use of alkali metals as promoters for the silver catalyzed production of ethylene oxide is extremely well known in the art. As far back as U.S. Pat. No. 2,177,361 issued October 1939 there is found a teaching of the use of alkali metals in silver catalysts. U.S. Pat. No. 2,238,471 discloses that lithium was very desirable as a promoter but that potassium and cesium were detrimental. The examples of that patent utilize essentially 10% by weight of potassium hydroxide or cesium hydroxide to the silver oxide employed in making the catalyst. Later, U.S. Pat. No. 2,404,438 stated that sodium and lithium were effective promoters for this reaction. Essentially the same teaching could be found in U.S. Pat. No. 2,424,084. U.S. Pat. No. 2,424,086 generalized about alkali metals as promoters and specified sodium in particular. In U.S. Pat. No. 2,671,764, the patentees believed that alkali metals in the form of their sulfates would be effective as promoters for such silver catalysts. In particular, the patentees stated that sodium, potassium, lithium, rubidium or cesium sulfates may be used as promoters. U.S. Pat. No. 2,765,283 described the pretreatment of a support with a dilute solution of a chlorine containing compound and indicated that such chlorine compounds should be inorganic. Particular illustrations cited of suitable inorganic chlorine compounds included sodium chloride, lithium chloride and potassium chlorate. This patent specified that the amount of the inorganic chlorine containing compound which is deposited on the catalyst support is from 0.0001% to 0.2% by weight, based on the weight of the support. U.S. Pat. No. 2,615,900 to Sears describes the use of metal halide in the treatment of the supported catalyst and specifies that such halides can be of alkali metals such as lithium, sodium, potassium, and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintain a moderate but steady activity of the catalyst over an extended period of time during normal operation. Thus, one particular metal halide treated catalyst would provide a short-term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials. U.S. Pat. No. 2,709,173 describes the use of a silver catalyst for making ethylene oxide in which there are provided simultaneously with the introduction of the silver catalyst to the solid support any of the alkali metal halides such as lithium, sodium, potassium, and rubidium compounds of chlorine, bromine and iodine, to enhance the overall production of ethylene oxide The patent specifies small amounts "of less than about 0.5% are desirable". In particular the patent emphasizes "proportions of alkali metal halide within the range of about 0.0001 to about 0.1%" are most preferred. The patent states that "although the preferred catalyst composition contains a separate promoter it is not always necessary since during preparation of the catalyst the alkali metal halide may be converted to some extent to the corresponding alkali metal oxide which acts as a promoter". U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate. U.S. Pat. No. 2,799,687 to Gould et al states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01-5 weight percent, preferably 0.01 to 0.1 weight percent, based on the weight of the "silver oxidative catalytic component", i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight, of metal oxide based on the weight of the support. U.S. Pat. No. 3,585,217 states that alkali metal chlorides "are known to counteract the formation of carbon dioxide" and "may be incorporated into the catalyst". U.S. Pat. No. 3,125,538 discloses a supported silver catalyst containing a coincidentally deposited alkali metal selected from among potassium, rubidium and cesium in a specified gram atom ratio relative to silver. The weight of silver is preferably 2-5% by weight, of the catalyst. The patentees characterize this catalyst as being especially suitable for the reaction of nitric oxide with propylene. U.S. Pat. Nos. 3,962,136 and 4,012,425 disclose the identical catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally combined with a minor amount of an oxide of potassium. The amount of such oxide is from about $4.0\times10^{-5}$ gew/kg to about $8.0\times10^{-3}$ gew/kg of total catalyst However, U.S. Pat. No. 4,010,115, patented Mar. 1, 1977, distinguishes itself by employing as the oxide of the alkali metal the oxide of potassium optionally combined with a minor amount of an oxide of rubidium or cesium. Application Ser. No. 317,349, filed Dec. 21, 1972, which is a parent to U.S. Pat. Nos. 3,962,136 and 4,010,115, and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide. Even so, we find that that amount of potassium in the catalyst lies within the range disclosed in U.S. Pat. No. 4,010,115 to be effective for the production of ethylene oxide, although no data is shown in the patent to support that view.

Belgium Patent No. 821,439, based upon British Patent Specification No. 1,489,335, discloses that a catalyst can be made that is equivalent to that produced in U.S. Pat. Nos. 3,962,136, 4,012,425, and 4,010,115 to Neilsen et al, by varying the procedure by which the alkali metal is supplied to the support. In the Belgium Patent and its British equivalent, a porous refractory support of a specified surface area is first impregnated with an alkali metal to deposit it on the support material in specified quantities (both the quantities and the nature of the porous support being equivalent to that which is set forth in the aforementioned Nielsen et al U.S. patents) the support is then dried to fix the alkali metal and thereafter the silver is supplied to the support. This procedure is a sequential deposition of the alkali metal promoter and the silver catalyst and yet essentially the same type of catalyst was produced by the simultaneous deposition of alkali metal and silver as evidenced by a comparison of the data in the examples of the Belgium Patent with the data set forth in the aforementioned Nielsen et al U.S. patents. The criticality in the method of deposition of alkali metal upon the support appears doubtful in the face of that type of disclosure and the disclosure of U.S. Pat. Nos. 4,033,903 and 4,125,480 which describe subjecting a used silver-containing catalyst with a post-addition of one or more of potassium, rubidium or cesium. Apparently such treatment regenerates the catalyst's ability to enhance selectivity to ethylene oxide. Another patent which tends to indicate that a post-addition of alkali metal such as cesium gives results equivalent to either pre-addition or simultaneous addition is U.S. Pat. No. 4,066,575.

U.S. Pat. No. 3,962,136 and its companion patents were derived from U.S. patent application Ser. No. 216,188, filed Jan. 7, 1972, now abandoned. U.S. Pat. No. 3,962,136 discloses that the "highest level of selectivity obtainable with potassium modified catalysts at other-wise comparable conditions typically is lower than that obtainable with rubidium or cesium-modified catalysts" (see column 2, lines 38-42). U.S. application Ser. No. 216,188 contains a drawing which depicts the relative effectiveness of rubidium, cesium and potassium to enhance the selectivity of ethylene oxide when utilized in a silver catalyst. The drawing shows that the curve C which represents cesium addition provides the greatest degree of enhancement of selectivity while curve B which represents rubidium addition is intermediate and superior to potassium addition represented by curve A. In an amendment filed on Apr. 11, 1975, in U.S. application Ser. No. 480,896, filed Jun. 19, 1974, which is a parent application to U.S. Pat. No. 4,010,115, the applicant urges that the invention and claims do not involve "synergistic effects with the use of mixtures" of the alkali metals. The same statement was made in the amendment received on Apr. 11, 1975 in U.S. patent application Ser. No. 471,398 filed May 20, 1974, which is the parent application to U.S. Pat. No. 4,012,425.

German Offenlegungsschrift No. 2,640,540 discloses in its examples a silver catalyst for ethylene oxide production containing sodium and either potassium, rubidium or cesium. Table I of this disclosure provides the alkali content of all catalysts prepared in the examples, many of which contain sodium, potassium and cesium. A footnote to the Table states that the presence of potassium in all catalysts tested (except for one which was free of cesium) was due to impurities present in the support, the level of such impurities being below that specified as being useful for the invention. The disclosure does not suggest that cesium may be combined with potassium and/or sodium to advantage nor does the efficiency data provided in the Table demonstrate a synergistic interaction of cesium with sodium or the potassium impurities in the catalysts.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples. No synergism with cesium and potassium was demonstrated by any of the cesium-potassium-barium mixtures of the examples. Indeed, a comparison of some examples among Table I appears to demonstrate the absence of a cesium-potassium synergism, namely, the efficiency achieved with a cesium-potassium mixture is shown to be lower than the efficiency achieved with the same amount of cesium in the absence of potassium. For example, Examples 3 and 7 relate to catalysts having an identical atomic ratio of cesium to silver (0.05 atoms/100 atoms Ag), but differing potassium contents, the atomic ratio of potassium in Example 3 being 0.001 atoms K/100 atoms Ag and the corresponding ratio in Example 7 being 0.05. The efficiency achieved in Example 3 was 76.4% and that of Example 7 was 75.9%. Thus, the increased potassium content in Example 7 resulted in a decrease in catalyst efficiency. Similarly, Examples 1 and 4 relate to catalysts having an identical atomic ratio of cesium to silver, with the catalyst of Example 1 containing an amount of potassium one order of magnitude greater than the catalyst of Example 4. Yet, the efficiencies reported for both catalysts are essentially the same, 76.7% and 76.6% for Examples 1 and 4, respectively.

U.S. Pat. No. 4,039,561 discloses a catalyst for preparing ethylene oxide containing silver, tin, antimony, thallium, potassium, cesium and oxygen in specified atomic ratios. Mixtures of cesium and potassium are not disclosed to be desirable combinations. Indeed, Table I of the patent discloses a silver-cesium-potassium combination which is designated as a "control" example not in accord with the disclosed invention and which achieved a selectivity of 73.0%, a value markedly lower than the selectivities achieved in the 45 Examples listed in Tables 2 and 3. Moreover, the efficiencies provided in Tables 2 and 3 for the various catalysts fail to demonstrate the existence of any synergistic combination of cesium and potassium among the numerous combination of elements which were employed in the catalysts. It is also note-worthy that the aforesaid U.S. Pat. No. 4,039,561 claims the priority of a Japanese application filed in 1973, and that subsequent to such filing the same applicant filed Japanese Application Publication No. 25703/77 which discloses a catalyst for ethylene oxide manufacture comprised of the same metallic elements disclosed in the U.S. patent with exception of cesium and potassium. The efficiencies disclosed in the examples of the latter Japanese Application are similar to those shown in the U.S. patent. The effect of cesium and potassium in the catalyst composition disclosed in the U.S. patent is therefore presumably insignificant.

Belgium Patent No. 854,904 discloses silver catalysts containing various mixtures of sodium and cesium. U.K. Patent Application No. GB 2,002252A discloses, in Table 2, supported silver catalysts containing various mixtures of cesium and thallium, some of which additionally contain potassium or antimony. U.S. Pat. No. 4,007,135 broadly discloses (in column 2, lines 25-30) silver catalysts for alkylene oxide production containing silver "together with a promoting amount of at least one promoter selected from lithium, potassium, sodium, rubidium, cesium, copper, gold, magnesium, zinc, cadmium, strontium, calcium, niobium, tantalum, molybdenum, tungsten, chromium, vanadium and barium . . . ". U.S. Pat. Nos. 3,844,981 and 3,962,285 disclose catalysts and processes for epoxidizing olefins in the presence of a multimetallic component. The catalyst in the U.S. Pat. No. 3,962,285 patent is said to comprise a minor amount of one or more of palladium, ruthenium, rhenium, iron and platinum with a major amount of silver. The U.S. Pat. No. 3,844,981 patent discloses the preparation of the catalyst from a decomposable salt of group 7b, 1b or the iron group of group 8 of the Periodic Table of the Elements. Preferably, the salt is selected from the group of gold, copper, rhenium, manganese and iron salts. While the patentee contemplates that these metals are in the metallic state, oxidation during epoxidation conditions may occur with one or more of these metals, e.g., rhenium, to form oxyanions containing the metal. European Patent Publication No. 0003642 discloses, in Table 3, silver-containing catalysts which include mixtures of potassium and cesium, and a catalyst containing sodium and cesium. The above publication do not indicate synergistic interaction of cesium with other alkali metals.

Belgium Patent No. 867,045 discloses supported silver catalysts containing what is referred to as an effective proportion of lithium and a substantially lesser amount of alkali metal selected from among cesium, rubidium and/or potassium. Table I of the patent discloses three catalysts all of which contain cesium, sodium, potassium and lithium, the lithium concentration being at least one order of magnitude greater than the concentration of cesium or potassium. Referring to Table I, the catalysts L1, L2 and L3 have markedly different concentrations of cesium, potassium and sodium, but are shown in Table II to provide substantially similar selectivities. There is no indication of a synergistic interaction of cesium with either potassium or sodium in the silver catalysts disclosed.

Belgium Patent No. 867,185 discloses supported silver catalysts for ethylene oxide production containing a specified amount of potassium and at least one other alkali metal selected from rubidium and cesium. United Kingdom Patent No. 2,043,481, commonly assigned, describes the use of a synergistic combination of cesium and at least one other alkali metal in combination with silver on an inert support to provide catalysts which were superior to those known to the art at that time. Such catalysts have been widely employed commercially. The alkali metal components are provided to the support by a variety of ways. The alkali metal can be supplied to the support as a salt and many salts of the alkali metals are described. Specific illustration is made of the use of alkali metal sulfates as one of many usable alkali metal compounds.

European Patent Application 85,237 describes an ethylene oxide catalyst wherein the applicants believe they "chemically absorbed" by alcohol wash, cesium and/or rubidium onto the catalyst support, a procedure not unlike that described by Neilsen and Schroer, supra. for potassium treated catalysts.

Japanese patent application Kokai 56/105,750 discloses, among other things, ethylene oxide catalysts containing cesium molybdate or cesium tungstate or cesium borate. The catalyst is stated to have an alumina carrier having a sodium content of less than 0.07 weight % and mainly consisting of alpha-alumina having a specific surface area of 1 to 5 sq. m/gm. The carrier is impregnated with decomposable silver salt solution containing alkali metal boron complex, alkali metal molybdenum complex and/or alkali metal tungsten complex. No examples of mixtures of anions are disclosed. Japanese patent application Kokai 57/21937 discloses thallium-containing catalysts in which the thallium may be borate or titanate salt.

A number of patent documents have been published relating to ethylene epoxidation catalysts which may contain oxyanions. European patent application 247,414, published Dec. 12, 1987, discloses catalysts containing alkali metal and/or barium which may be provided as salts. The salts include nitrates, sulfates, and halides. European patent applications 266,015, published May 4, 1988, and 266,852, published May 11, 1988, disclose catalysts containing a rhenium component, e.g., rhenium oxide, rhenium cation or rhenate or perrhenate anion. An example of a catalyst made from silver oxalate with cesium hydroxide, ammonium perrhenate, and ammonium sulfate is disclosed in the '852 application. Numerous examples of silver catalysts containing cesium, rhenate and co-promoter salts are presented in the '015 application. For instance, Experiment 7-12 reports a catalyst having 13.5 weight percent silver, 338 ppmw (parts per million by weight) cesium (CsOH) 186 ppmw rhenium ($NH_4ReO_4$) and 55 ppmw manganese ($KMnO_4$), experiment 7-6, 12.7 wt %, 421 ppm cesium, 186 ppmw rhenium, 32 ppm sulfur (($NH_4)_2SO_4$); and Experiment 7-26, 14.7 wt % silver, 387 ppmw cesium and 78 ppmw potassium (as sulfate), 186 ppmw rhenium, 32 ppmw sulfur (($NH_4)_2SO_4$), and 184 ppmw tungsten ($H_2WO_4$). Experiments are presented in which vanadate, chlorate, molybdate, chromate, sulfite, phosphate and tungstate anion are added in combination with rhenate anion.

In U.S. Pat. No. 4,916,243, the inventor discovered that a mixture of particular cesium salts in combination with at least one alkali from Rb, K, Na, Li, achieves a greater (higher selectivity) synergistic result than prior catalysts containing only cesium. U.S. Pat. No. 4,908,343 patent, the inventor discovered further improvements in catalyst performance of impregnated silver on a support when using a mixture of cesium salt and one or more alkali metal and alkaline earth metal salts in which the anions thereof are halide or oxyanions of elements other than the oxygen therein having an atomic number of 7 or 15 to 83 and being from groups 3b through 7b, inclusive, and 3a through 7a, inclusive, of the Periodic Table of the Elements, at least a portion of said oxyanions are oxyanions of group 3b to 7b elements. In another related patent, U.S. Pat. No. 5,057,481, the same inventor also discovered performance improvements using impregnated silver on a support and a mixture of cesium salts, at least one of which is a cesium salt in which the anions thereof are oxyanions of elements having an atomic number of 2i to 75 and being from groups 3b through 7b, inclusive, of the Periodic Table of the Elements.

Further, in U.S. Pat. Nos. 4,761,394, 4,766,105, 4,808,738, 4,820,675 and 4,833,261, the inventor therein describes an ethylene oxide catalyst including silver, a promoting amount of alkali metal, and a promoting amount of rhenium supported on a support having an aluminous composition.

Catalyst supports for selective oxidations or exothermic reactions, in general, are relatively low surface area of the order of about 10 m$^2$/g surface area or preferably about 5 m$^2$/g surface area, and pore volumes of about 1 cc/g and more typically 0.7 cc/g. Furthermore, the purity of such supports should be about 95%, preferably 99%, of the predominant compositions. High purity supports are critical to making catalysts providing high selectivity to the desired products that are typically intermediates in the reaction.

One such product is ethylene oxide produced by selective oxidation of ethylene to ethylene oxide while minimizing the formation of undesirable combustion products, namely carbon dioxide. Worldwide production of ethylene oxide is upwards of 25 million metric tons per year, and hence of great industrial importance. Desired ethylene oxide product selectivity at commercially viable production rates is typically 90% using the alpha-alumina based supports.

Other valuable products include olefins, nitriles, acids and other desired products deriving from the selective oxidation of ethane and other desired products from oxidative coupling of methane. Likewise, products from exothermic hydrogenation reactions and hydrodesulfurizations of various light and heavy hydrocarbon feed stocks can be produced from high purity catalysts. Similarly, high purity supports are also beneficial for endothermic reactions, such as dehydrogenation of various paraffins, very important industrial reactions such as propane, butanes, and higher linear paraffins, C-9 to C-14; dehydrogenation of ethyl benzene to styrene; and cracking and hydrocracking of heaver hydrocarbons to lighter ones for fuels.

Prior art has relied almost entirely on compositions containing primarily alpha-alumina, with or without certain binders, typically having purity of <95% and certainly <99%. This prior technology provides for selective oxidation of ethylene to ethylene oxide over a catalyst based on silver and a combination of promoters comprising Re, S, alkali metals, Cs, Rb, K, Na, Li and/or W, Mo, etc., supported on an alpha-alumina support. Although over a thousand patents have issued since the discovery by Theodore Emile LeFort's discovery that ethylene oxide can be catalytically prepared directly from ethylene and oxygen over silver, it has not been appreciated in the art that a high purity, porous silicon carbide, having about 10 m$^2$/g or preferably 5 m$^2$/g surface area, and 1 cc/g pore volume can provide >90%, or >92% or >95% selectivity to ethylene oxide, heretofore not achievable at commercial production rates of 10 lb/ft$^3$/hr of EO.

While prior art catalyst supports have from time to time included SiC in the support composition, the prior art failed to recognize the importance of high purity SiC 95%, preferably 99%) catalyst supports, capable of achieving high porosity, high surface area compositions that have not heretofore existed. Instead, the SiC containing compositions of the prior art were tried, but they contained 10-20+% of various clays as binders such that the SiC was totally covered up by the clay constituents (e.g., Na, K, Ca, Mg silicates or aluminosilicates). The clays are added to act as binding agents for SiC since they melt at 1000-1300° C. much below the sintering temperature of SiC (2000° C.). Moreover, such highly impure SiC supports had very low surface areas, typically <0.1 m$^2$/g. Hence, silver catalyst and promoter components were located on the clay phase and never touched the SiC composition.

Novel catalyst supports of the disclosed technology include silicon carbide alone or in mixtures with other carbides, borides or nitrides, and can provide selectivity to the ethylene oxide desired product at commercial rates, the selectivity being >90%, or >92%, or >95%. These novel catalyst supports are also beneficial for other selective oxidation reactions, such as oxydehydrogenation of ethane, propane to produce corresponding olefins, nitriles, acids, etc., methane oxidative coupling to make ethylene, propylene, ethane, and other desired products. While not wishing to be bound by theory, thermal conductivity of silicon carbide (Watts/m/k) is believed to be at least a factor 10-100 greater than that for alpha-alumina (with the removal of exothermic heat, this should lead to higher efficiency). The novel supports provided by means of the disclosed technology have desirable surface area, pore volume and the high purity. The combination of higher thermal conductivity properties and high purity with desirable surface area, pore volume and strength, provide high selectivity of >90%, >92% and/or >95% to ethylene oxide when reacting ethylene with 02 in typical ethylene oxide process conditions, including the gas phase chloride promoter.

GENERAL DESCRIPTION

The disclosed technology regards a catalyst support having at least about 90%, or in some embodiments at least about 95%, silicon carbide, having surface areas of about 10 m$^2$/g and pore volumes of about ≤1 cc/g. For purposes of this disclosure, the term "about" means within 2-5% of the stated value.

The disclosed technology further regards a method of producing a catalyst support, the method including (1) mixing SiC particles of 0.1-20 microns, SiO$_2$ and carbonaceous materials to form an extrusion, (2) under inert atmospheres, heating the extrusion at temperatures of greater than about 1400° C.-2000° C., and (3) removing residual carbon from the heated support under temperatures below 1000° C.

The disclosed technology further regards a catalyst on a carrier, comprising a carrier support having at least about 90%, or about 95% SiC, with a silver solution impregnated thereon including silver oxide, ethylenediamine, oxalic acid, monoethanolamine and cesium hydroxide.

The disclosed technology further regards a process for selective oxidation of ethane, ethylene, propane, and methane, to produce valuable products such as, for example, the production of ethylene oxide, using ethylene and 02 as reactants over a catalyst support comprising at least about 95% SiC, impregnated with silver. Another suitable use of the catalyst supports of the disclosed technology is in the exothermic hydrogenation reactions and hydrodesulfurizations of various light and heavy hydrocarbon feed stocks. Similarly, the novel catalyst supports are also beneficial for endothermic reactions, such as dehydrogenation of various paraffins, very important industrial reactions such as propane, butanes, and higher linear paraffins, C-9 to C-14; dehydrogenation of ethyl benzene to styrene; and cracking and hydrocracking of heaver hydrocarbons to lighter ones for fuels.

DETAILED DESCRIPTION

The catalyst support of the disclosed technology includes silicon carbide (SiC) mixed with a carbon source to make an extrudable mixture to form tablets, spheres or rings, or other shapes. The shaped mixture is then placed in a furnace having an inert gas, such as Argon, Helium, or less desirably nitrogen. The temperature of the furnace is gradually increased to above 1000° C., or 1200° C. or 1400° C.-1800° C., well below the sintering temperature of SiC (2000° C.). Alternatively, the catalyst support composition can be prepared by sintering higher surface area phases such as β-SiC composition, using known methods. During any of these high-heat processes, the particles in aggregate form begin to bind together with the formation of SiC at the interfaces of the SiC particles.

Although some silica ($SiO_2$) will be naturally present within the SiC—C mixture, suitable small amounts of $SiO_2$ may be added to the SiC—C mixture, up to its stoichiometric ratio with the carbon. The addition of $SiO_2$ to the mixture facilitates the self-binding of the material. The $SiO_2$ and the carbon source react to form finer SiC by the following reaction:

$$SO_2 + C \rightarrow SiC + CO$$

Finally, the remaining organic carbon is burnt away at temperatures below 1000° C., such as below 800° C. or 600° C., resulting in a very-high purity silicon carbide catalyst support.

The silicon carbide used in the catalyst support of the disclosed technology should include very-high purity (99+ %, or 99.5%, or 99.9%) α-SiC, having particle sizes of 0.1-1 microns; this fine particle size α-SiC may be mixed with very high purity α-SiC having one or more larger particles sizes of 1-10 microns, such as for example α-SiC having particle sizes of 1-5 microns and α-SiC having particle sizes of 5-10 microns. An exemplary mixture of SiC particles suitable for use in the disclosed technology is 0.1-1 microns α-SiC, 1-5 microns α-SiC, and 5-10 microns α-SiC, wherein the selection of ratio of particles would depend on desired porosity and pore value of the catalyst support. β-SiC having varying particle sizes may also be used in the catalyst support of the disclosed invention.

The carbon source used in the catalyst support of the disclosed technology may be one more carbon sources, such as high purity (99+%) organic polymers and graphite, as well as traditional, pure, pore formers, such as cellulose, starch, synthetic polymers such as polyacrylates and polyethylenes, and combinations thereof. Carbides, borides, and nitrides may also be used in the SiC—C mixture for strengthening the support, and increasing the thermal conductivity of the support. In an exemplary embodiment, the mixture comprises 30-60% w/w pore formers; and a carbon source in a stoichiometric ratio of 1:1 ratio with the SiC (notably, some carbon could be supplied from the pore formers).

A liquid such as water or an acid, such as an organic add, including acetic acids, is added to the SiC—C mixture to make the extrudable mixture; this liquid evaporates during the heating of the pellets as hereinabove described.

Catalyst supports made using the foregoing methods have good strength (at least 10 lbs side crushed), a high purity, porous silicon carbide, with about 10 m²/g or preferably ≤5 m²/g surface area, and ≤1 cc/g pore volume or more preferably 0.7 cc/g, which when impregnated with the catalyst can provide >90%, or >92% or >95% selectivity to ethylene oxide, heretofore not achievable at commercial production rates of 10 lb/ft³/hr of EO.

A variety of procedures may be employed for preparing catalysts containing silver and combinations of cesium and one or more other alkali metals (excluding francium) in accordance with the disclosed technology. The preferred procedure comprises: (1) impregnating a porous catalyst carrier with a solution comprising a solvent or solubilizing agent, silver salt in an amount sufficient to deposit the desired weight of silver upon the carrier, and salts of (a) cesium and (b) at least one other alkali metal selected from the group consisting of lithium, sodium, potassium and rubidium sufficient to deposit respective amounts of (a) and (b) on the support such that the efficiency of ethylene oxide manufacture of the finished catalyst is increased to a value greater than the efficiencies obtainable under common conditions from respective catalysts which are the same as said catalyst except that instead of containing both (a) and (b), one contains the respective amount of (a), and the other contains the respective amount of (b); and thereafter (2) treating the impregnated support to convert at least a fraction of the silver salt to silver metal and effect deposition of silver, (a) and (b), respectively, on the support surface. Silver and alkali metal deposition are generally accomplished by heating the carrier at elevated temperatures to evaporate the liquid within the support and effect deposition of the silver and alkali metal onto the interior and exterior carrier surfaces. Alternatively, a coating of silver and alkali metals may be formed on the carrier from an emulsion or slurry containing the same followed by heating the carrier as described above. Impregnation of the carrier is generally the preferred technique for silver deposition because it utilizes silver more efficiently than coating procedures, the latter being generally unable to effect substantial silver deposition onto the interior surfaces of the carrier. In addition, coated catalysts are more susceptible to silver loss by mechanical abrasion.

The sequence of impregnating or depositing the surfaces of the carrier with silver and alkali metals is optional. Thus, impregnation and deposition of silver and alkali metals may be effected coincidentally or sequentially, i.e., the alkali metals may be deposited prior to, during, or subsequent to silver addition to the carrier. The alkali metals may be deposited together or sequentially. For example, cesium may be deposited first followed by the coincidental or sequential deposition of silver and the other alkali metal(s), or such other alkali metal(s) may be deposited first followed by coincidental or sequential deposition of silver and cesium.

Impregnation of the catalyst carrier is effected using one or more solutions containing silver and alkali metal compounds in accordance with well-known procedures for coincidental or sequential depositions. For coincidental deposition, following impregnation the impregnated carrier is heat or chemically treated to reduce the silver compound to silver metal and deposit the alkali metals onto the catalyst surfaces. For sequential deposition, the carrier is initially impregnated with silver or alkali metal (depending upon the sequence employed) and then heat or chemically treated as described above. This is followed by a second impregnation step and a corresponding heat or chemical treatment to produce the finished catalyst containing silver and alkali metals.

The silver solution used to impregnate the carrier is comprised of a silver salt or compound in a solvent or complexing/solubilizing agent such as the silver solutions disclosed in the art. The particular silver salt or compound employed is not critical and may be chosen, for example, from among silver nitrate, silver oxide or silver carboxylates, such as, silver acetate, oxalate, citrate, phthalate, lactate, propionate, butyrate and higher fatty acid salts.

A wide variety of solvents or complexing/solubilizing agents may be employed to solubilize silver to the desired concentration in the impregnating medium. Among those disclosed in the art as being suitable for this purpose are lactic acid (U.S. Pat. No. 2,477,435 to Aries; and U.S. Pat. No. 3,501,417 to DeMaio); ammonia (U.S. Pat. No. 2,463,228 to West et al); alcohols, such as ethylene glycol (U.S. Pat. No. 2,825,701 to Endler et al; and U.S. Pat. No. 3,563,914 to Wattimena); and amines and aqueous mixtures of amines (U.S. Pat. No. 2,459,896 to Schwarz; U.S. Pat. No. 3,563,914 to Wattimena; U.S. Pat. No. 3,702,259 to Nielsen; and U.S. Pat. No. 4,097,414 to Cavitt).

Suitable alkali metal salts include all those soluble in the particular solvent or solubilizing agent employed. Accordingly, inorganic and organic salts of alkali metals, such as, nitrates, halides, hydroxides, sulfates and carboxylates may be used. When coincidentally deposited with silver, the alkali metal salt employed is preferably one which does not react with silver salt in solution in order to avoid premature silver precipitation from same. Thus, for example alkali metal halides are preferably not used in lactic acid solution because they react with silver ions present therein.

Following impregnation of the catalyst carrier with silver and alkali metal salts, the impregnated carrier particles are separated from any remaining non-absorbed solution or slurry. This is conveniently accomplished by draining the excess impregnating medium or alternatively by using separation techniques, such as, filtration or centrifugation. The impregnated carrier is then generally heat treated (e g., roasted) to effect decomposition and reduction of the silver metal salt to metallic silver and the deposition of alkali metal ion. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry but not roast reduce the catalyst. U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range) it is only important that the reduction time be correlated with temperature such that substantially complete reduction of the silver salt to metal is accomplished. A continuous or stepwise heating program may be used for this purpose.

Heat treatment is preferably carried out in air, but a nitrogen or carbon dioxide atmosphere may also be employed. The equipment used for such heat treatment may use a static or flowing atmosphere of such gases to effect reduction.

The particle size of silver metal deposited upon the carrier is a function of the catalyst preparation procedure employed. Thus, the particular choice of solvent and/or complexing agent, silver salt, heat treatment conditions and catalyst carrier may affect, to varying degrees, the size of the resulting silver particle. For carriers of general interest for the production of ethylene oxide, a distribution of silver particle sizes in the range of 0.05 to 2.0 microns is typically obtained. However, the role of particle size of the silver catalyst upon the effectiveness of the catalyst in making ethylene oxide is not clearly understood. In view of the fact that the silver particles are known to migrate on the surface of the catalyst when used in the catalytic reaction resulting in a marked change in their size and shape, silver particle size may not be a significant factor in affecting catalytic performance.

The concentration of silver in the finished catalyst may vary from about 2 to 40 weight percent, the preferred range being from about 6% to about 30% by weight of silver. Lower silver concentrations are preferred from an economic standpoint. However, the optimum silver concentration for any particular catalyst will be dependent upon economic factors as well as performance characteristics, such as catalyst efficiency, rate of catalyst aging and reaction temperature.

The concentration of cesium salt and any other alkali metal and alkaline earth metal salts in the finished catalyst is not narrowly critical and may vary over a wide range. The optimum cesium salt and other salt concentration for a particular catalyst will be dependent upon performance characteristics, such as, catalyst efficiency, rate of catalyst aging and reaction temperature. The concentration of cesium salt in the finished catalyst may vary from about 0.0005 to 1.0 weight percent, preferably from about 0.005 to 0.1 weight percent. Cesium salts alone, or together with at least one other alkali or alkaline earth metal salt, can be employed in the finished catalyst. The ratio of cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably about 20 to 100, percent (weight) of the total added alkali metal and alkaline earth metal in the finished catalyst.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as, temperature, pressure, residence time, concentration of reactants, diluents (e.g., nitrogen. methane and $CO_2$), inhibitors (e.g., ethylene dichloride) and the like. In addition, the desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the process is carried out by continuously introducing a feed stream containing ethylene and oxygen to a catalyst-containing reactor at a temperature of from about 200° to 300° C., and a pressure which may vary from one atmosphere to about 30 atmospheres depending upon the mass velocity and productivity desired. Residence times in large-scale reactors are generally on the order of about 1-5 seconds. Oxygen may be supplied to the reaction in an oxygen-containing stream, such as, air or as commercial oxygen. The resulting ethylene oxide is separated and recovered from the reaction products using conventional methods.

Likewise, suitable catalysts of the disclosed technology are useful in other selective oxidation reactions, such as ethane oxydehydrogenation of ethane, propane to produce corresponding olefins, nitriles, acids, etc., methane oxidative coupling to make ethylene, propylene, ethane, and other desired products. Similarly, suitable catalysts of the disclosed technology are useful in the exothermic hydrogenation reactions and hydrodesulfurizations of various light and heavy hydrocarbon feed stocks, and for endothermic reactions, such as dehydrogenation of various paraffins, very important industrial reactions such as propane, butanes, and higher linear paraffins, C-9 to C-14; dehydrogenation of ethyl benzene to styrene; and cracking and hydrocracking of heaver hydrocarbons to lighter ones for fuels.

In experimentation, a heat treated α-SiC support of the disclosed technology was impregnated under vacuum conditions with a silver solution of 1.534 g/cc, and calcined at 350° C. for 8 minutes. The performance of four separately prepared catalyst examples were then tested in a ¼ inch tubular reactor with a gaseous mixture of: 25% ethylene, 7% oxygen, 2% carbon dioxide and the balance nitrogen and ppm quantity addition of ethyl chloride (1-10 ppm) and ethane (0-5% molar concentration). The preparation and performance of the catalyst examples follow.

The four catalysts containing 19 wt. % silver (Ag) and, respectively, 0.00, 0.005, 0.010, and 0.015 wt % cesium (Cs) were prepared on the high purity α-SiC support of the disclosed technology having a chemical composition of: α-SiC=99.9%, silicon dioxide <400 ppm, with a surface area of 1.7 m²/g, and a pore volume of 0.51 cc/g. The impregnated α-SiC support was placed in an oven with its temperature ramped to and held at 650° C. for 14 hours, and then allowed to cool.

The silver solution was prepared from: 56.695 g deionized water, 36.945 g ethylenediamine (99.5% specification purity), 37.577 g oxalic acid (99.6% specification purity), 64.145 g silver oxide (99.7% specification purity), 12.959 g monoethanolamine (98% specification purity), and cesium hydroxide (99.95% specification purity) is added at 0.031 g of 10.27% aqueous solution added to 45.01 g of prepared silver solution to achieve 50 ppm on the final catalyst.

The silver solution was prepared in a beaker with available cooling by means of an ice bath to manage the temperature of the solution within the range of 35°-40° C., constant stirring, and temperature measurement. The solution was prepared starting with the deionized water, stirred with small additions of ethylene diamine, oxalic acid, monoethanolamine, and cesium hydroxide to ensure that the temperature is controlled within bounds mentioned above. The remainder of the ethylenediamine was added to the solution, followed by the oxalic acid until all of the oxalic acid was dissolved. Next, the silver oxide was added until all of the silver oxide was dissolved. Thereafter, monoethanolamine was added, and the solution is then promptly filtered with 1.5 micron borosilicate glass microfiber filter paper while the solution was warmer than 30° C. The final solution was clear with a slight amber color. The amount of silver solution was applied to the support to achieve the target catalyst concentration.

The solution was prepared at a concentration such that the desired amount of silver and cesium were obtained in the final catalyst, for each exemplary catalyst, wherein the required solution was calculated for the given catalysts from the packing density and pore volume of the support, assuming that all of the metals contained in the pore volume are deposited on the support after calcination of the impregnated support. The catalyst compositions were calculated based on weight gained by the support (almost entirely due to silver deposited on the support), and the ratios to silver concentration in solution.

For impregnating the support with the catalyst, the heat treated α-SiC support was placed into a vacuum separator funnel. The vacuum separator funnel is connected to a vacuum pump with shutoff valve and to a separator funnel containing the silver solution to facilitate addition of the silver solution after the vacuum is established. The vacuum separator funnel containing the support was evacuated by means of the vacuum pump to achieve 30 mm Hg absolute pressure and held for 5 minutes. The silver solution was then added to the flask while vacuum is maintained and until the catalyst support is completely covered by solution. The vacuum valve is then closed, and the separator funnel containing the support and added silver solution is then allowed to return to atmospheric pressure. All of the free liquid is drained from the vacuum container and free moisture is removed from the catalyst surface by use of a damp paper towel. The impregnated silicon carbide support is then ready for calcination.

Calcination of the impregnated support was performed in a tubular oven with air flow upwards across the catalyst that has been arranged in a single layer in a wire mesh basket. The impregnated support was place in a part of the oven was constructed of 2" stainless steel pipe with a heating zone controlled by a clamshell heater. The heating zone for calcination of the catalyst was constructed of a stainless steel piping tee with a wire grate the bottom of the tee to hold the catalyst basket and a finer wire mesh screen covering the top of the tee for radiant heat to the top of the catalyst. The middle of the tee (facing horizontally) was open for insertion of the wire mesh basket containing the impregnated support and was covered with insulation during the calcination process to maintain the temperature. The air flow through the heater to the heating zone is 80 standard cubic feet per hour (SCFH). The heating zone temperature was measured and allowed to stabilize at 350° C. Once the heating zone was stabilized, the impregnating support was placed into the heating zone and the opening is covered with insulation. The calcination was performed at 350° C. for 8 minutes and removed promptly to cool.

The catalyst was prepared for testing in the ¼"×36" tubular reactor tests by crushing with mortar and pestle and sieved to 12-14 mesh. The catalyst was loaded into the ¼" tube reactors with 8.34 g of catalyst (17.5 inches) on top of 12 g of inert support (12 inches). 25% ethylene, and 7% oxygen, and 2% carbon dioxide, and balance of nitrogen, were fed into the reactor at operation temperatures of 200° to 270° C. Ethyl chloride (ECL) in nitrogen was added to achieve ppm quantity concentrations of ECL in the feed and similarly ethane was added to the feed at 0.5 mol %. Inlet and outlet compositions were monitored by mass spectrometer. Selectivity of EO was calculated based on inlet and outlet compositions were measured in 5 minute intervals.

The reaction was started at 220° C. and was increased stepwise over 150 hours to a final temperature of 255° C. During this time ECL concentrations were varied and selectivity monitored to find the optimum range for selectivity and activity of the catalyst. Activity of the catalyst increased over this period as measured by delta EO increasing from 0.3% to 1.5%.

The next phase of the study examined the effect of ECL on the catalyst by varying the concentration from 0.1 ppm to 1.5 ppm while holding the reaction temperature at 255° C. for a duration of 200 hrs. The final 100 hrs. of the run were conducted at 255° C. and with ethylene chloride at a level determined in the earlier part of the run to achieve an optimal delta EO composition and selectivity.

The performance of the catalysts were measured by a mass spectrometer and material balance were calculated. The inlet and outlet compositions of nitrogen, ethylene, oxygen, carbon dioxide, and ethylene oxide were also measured by a mass spectrometer, and the water composition was calculated by material balance. Ethane was measured by flow and was not calibrated in the mass spectrometer. The material balance for carbon was 0.95 (with ethane interferences; without ethane in the feed material balances were near 1.0 in earlier tests) with a standard deviation of 0.016 for 600 observations. The material balance for oxygen was 1.01 with a standard deviation of 0.013 for 600 observations.

The mean performance of the catalysts in examples 1-4 for 2 days with 150 observations at stable conditions are set forth below:

| Catalyst example | Cesium Content ppm | ECL in feed ppm | % Ethane | Selectivity Mean | Selectivity Max | Std Dev Selectivity | Delta EO at conditions ECL concentration | Std Dev Delta EO |
|---|---|---|---|---|---|---|---|---|
| 1 | 0 | 0.7 | 0.5 | 72.3 | 72.9 | 0.2 | 0.88 | 0.02 |
| 2 | 50 | 0.8 | 0.5 | 72.2 | 73.3 | 0.3 | 0.80 | 0.01 |
| 3 | 100 | 1.1 | 0.5 | 72.8 | 73.3 | 0.2 | 0.79 | 0.04 |
| 4 | 150 | 0.7 | 0.5 | 71.3 | 71.8 | 0.3 | 0.80 | 0.01 |

The invention claimed is:

1. A method of producing a catalyst support, the method comprising:
   a. mixing silicon carbide particles of 0.1-20 microns, silicon dioxide and carbonaceous materials to form an extrusion,
   b. under inert atmospheres, heating the extrusion at temperatures of greater than 1400° C. to form the catalyst support, and
   c. removing residual carbon from the heated catalyst support under temperatures below 1000° C.

2. The method of producing a catalyst support of claim 1, wherein the silicon carbide particles are selected from a combination of particle sizes, some of which are 0.1-1 microns, some of which are 1-5 microns, and some which are 5-10 microns.

3. The method of producing a catalyst support of claim 1, wherein the extrusion is heated in the presence of argon or helium.

* * * * *